(12) United States Patent
Varela

(10) Patent No.: US 8,795,366 B2
(45) Date of Patent: *Aug. 5, 2014

(54) EXPANDABLE INTERVERTEBRAL IMPLANT AND ASSOCIATED SURGICAL METHOD

(75) Inventor: Armando Varela, Boca Raton, FL (US)

(73) Assignee: Innova Spinal Technologies, LLC, Boca Raton, FL (US)

( * ) Notice: Subject to any disclaimer, the term of this patent is extended or adjusted under 35 U.S.C. 154(b) by 354 days.

This patent is subject to a terminal disclaimer.

(21) Appl. No.: 12/974,511

(22) Filed: Dec. 21, 2010

(65) Prior Publication Data

US 2011/0172774 A1 Jul. 14, 2011

Related U.S. Application Data

(60) Provisional application No. 61/293,997, filed on Jan. 11, 2010, provisional application No. 61/296,932, filed on Jan. 21, 2010.

(51) Int. Cl.
*A61F 2/44* (2006.01)
*A61F 2/46* (2006.01)
*A61F 2/30* (2006.01)

(52) U.S. Cl.
CPC ....... *A61F 2/447* (2013.01); *A61F 2002/30551* (2013.01); *A61F 2002/30281* (2013.01); *A61F 2002/30522* (2013.01); *A61F 2002/30538* (2013.01); *A61F 2002/30556* (2013.01); *A61F 2002/30387* (2013.01); *A61F 2002/30579* (2013.01); *A61F 2002/30507* (2013.01); *A61F 2002/30841* (2013.01); *A61F 2002/30878* (2013.01); *A61F 2/4611* (2013.01)
USPC ....................................................... 623/17.11

(58) Field of Classification Search
USPC .................... 623/17.11–17.16; 606/279, 246, 606/248–249
See application file for complete search history.

(56) References Cited

U.S. PATENT DOCUMENTS 6,080,193 A 6/2000 Hochshuler et al.
6,102,950 A * 8/2000 Vaccaro ................. 623/17.16
(Continued)

FOREIGN PATENT DOCUMENTS

WO WO2006045094 A2 4/2006
WO WO2006113080 A2 10/2006
WO WO2008044057 A1 4/2008
WO WO2011047230 A1 4/2011

*Primary Examiner* — Ellen C Hammond
*Assistant Examiner* — Michelle C Eckman
(74) *Attorney, Agent, or Firm* — Clements Bernard PLLC; Christopher L. Bernard; Lawrence A. Baratta, Jr.

(57) ABSTRACT

The present invention provides an expandable intervertebral implant that is selectively disposed in the intervertebral space and deployed, thereby in-situ distracting, realigning, and/or stabilizing or fusing a portion of the spine of a patient in the treatment of injury, disease, and/or degenerative condition. The expandable intervertebral implant includes a superior member and an inferior member, each of which has a partially or substantially wedge or prismatic shape and a partially or substantially convex or other-shaped surface that is suitable for engaging the substantially concave surfaces of the associated bony superior and inferior intervertebral endplates. Once disposed in the intervertebral space, the expandable intervertebral implant is actuated and deployed, with the superior member and the inferior member moving apart from one another, seating against the associated intervertebral endplates, and distracting, realigning, and/or stabilizing them to a desired degree. The external surface of each of the superior member and the inferior member is provided with a plurality of ridges or other friction structures, providing purchase with the associated intervertebral endplates.

9 Claims, 22 Drawing Sheets

(56) References Cited

U.S. PATENT DOCUMENTS

| | | |
|---|---|---|
| 6,126,689 A | 10/2000 | Brett |
| 6,454,807 B1 | 9/2002 | Jackson |
| 6,685,742 B1 | 2/2004 | Jackson |
| 6,706,070 B1 | 3/2004 | Wagner et al. |
| 6,835,206 B2 | 12/2004 | Jackson |
| 7,066,961 B2 | 6/2006 | Michelson |
| 7,217,293 B2 | 5/2007 | Branch, Jr. |
| 7,569,074 B2 | 8/2009 | Eisermann et al. |
| 7,771,473 B2 | 8/2010 | Thramann |
| 7,850,733 B2 | 12/2010 | Baynham et al. |
| 2003/0065396 A1* | 4/2003 | Michelson ................. 623/17.15 |
| 2005/0131536 A1 | 6/2005 | Eisermann et al. |
| 2005/0177235 A1* | 8/2005 | Baynham et al. .......... 623/17.11 |
| 2005/0209698 A1 | 9/2005 | Gordon et al. |
| 2005/0278026 A1 | 12/2005 | Gordon et al. |
| 2006/0247770 A1 | 11/2006 | Peterman |
| 2007/0270968 A1* | 11/2007 | Baynham et al. .......... 623/17.11 |
| 2007/0276498 A1* | 11/2007 | Aebi et al. ................. 623/17.16 |
| 2008/0140207 A1* | 6/2008 | Olmos et al. ............... 623/17.16 |
| 2008/0147193 A1* | 6/2008 | Matthis et al. ............. 623/17.16 |
| 2009/0024217 A1 | 1/2009 | Levy et al. |
| 2009/0222100 A1 | 9/2009 | Cipoletti et al. |
| 2009/0292361 A1* | 11/2009 | Lopez ....................... 623/17.15 |
| 2010/0211176 A1* | 8/2010 | Greenhalgh ............... 623/17.15 |
| 2010/0222816 A1 | 9/2010 | Gabelberger et al. |
| 2010/0222884 A1* | 9/2010 | Greenhalgh ............... 623/17.11 |
| 2010/0292796 A1* | 11/2010 | Greenhalgh et al. ....... 623/17.11 |
| 2011/0015742 A1* | 1/2011 | Hong ........................ 623/17.11 |
| 2011/0054621 A1* | 3/2011 | Lim .......................... 623/17.16 |
| 2011/0093074 A1 | 4/2011 | Glerum et al. |
| 2012/0059475 A1* | 3/2012 | Weiman ..................... 623/17.16 |
| 2012/0203347 A1* | 8/2012 | Glerum et al. ............. 623/17.16 |

* cited by examiner

EXPANDABLE INTERVERTEBRAL IMPLANT AND ASSOCIATED SURGICAL METHOD

CROSS-REFERENCE TO RELATED APPLICATION(S)

The present patent application/patent claims the benefit of priority of U.S. Provisional Patent Application No. 61/293,997, filed on Jan. 11, 2010, and entitled "EXPANDABLE INTERVERTEBRAL BODY STABILIZATION DEVICES AND ASSOCIATED SURGICAL METHODS" and U.S. Provisional Patent Application No. 61/296,932, filed on Jan. 21, 2010, and entitled "EXPANDABLE INTERVERTEBRAL BODY STABILIZATION DEVICES AND ASSOCIATED SURGICAL METHODS," the contents of both of which are incorporated in full by reference herein.

FIELD OF THE INVENTION

The present invention relates generally to minimally-invasive, surgically-implantable spinal devices and systems. More specifically, the present invention relates to an expandable intervertebral implant that is surgically implanted to, in-situ distract, realign, and/or stabilize or fuse a portion of the spine of a patient in the treatment of injury, disease, and/or degenerative condition. Exemplary indications include, but are not limited to, spinal stenosis, degenerative disc disease with a loss of disc height, disc herniation, spondylolisthesis, retrolisthesis, and disogenic back pain. This expandable intervertebral implant may be surgically implanted via an open or, more preferably, minimally-invasive surgical procedure. Advantageously, the expandable intervertebral implant has a very small undeployed cross-section or footprint due to the use of superior and inferior members that nest against one another in a novel manner.

BACKGROUND OF THE INVENTION

In various cases, it is desirable to restore the anatomic relationship between various vertebral elements, thereby re-establishing spinal stability, by means other than conventional monolithic and/or multi-piece interbody spacers. Typically, these devices require sizable working channels, soft tissue disruption, nerve root retraction, and significant bone resection, thereby increasing the resulting stress on other vertebral elements. Further, morbidities associated with these more-invasive procedures include, but are not limited to, greater blood loss, longer recovery, and increased risk of surgical site infection.

In such cases, the use of an alternative intervertebral implant, especially one compatible with minimally-invasive surgical techniques, is desirable. An intervertebral implant that expands in-situ would allow implantation without the iatrogenic insult that is commonly associated with the implantation of conventional monolithic and/or multi-piece interbody spacers in a minimally-invasive manner. However, no such alternative devices or systems are currently available, at least not any that are adequate.

BRIEF SUMMARY OF THE INVENTION

In various exemplary embodiments, the present invention provides an expandable intervertebral implant that is selectively disposed in the intervertebral space and deployed, thereby in-situ distracting, realigning, and/or stabilizing or fusing a portion of the spine of a patient in the treatment of injury, disease, and/or degenerative condition. The expandable intervertebral implant includes a superior member and an inferior member, each of which has a partially or substantially wedge or prismatic shape and a partially or substantially convex or other-shaped surface that is suitable for engaging the substantially concave surfaces of the associated bony superior and inferior intervertebral endplates. Optionally, the superior member and the inferior member are each thinner at the leading edge of the expandable intervertebral implant than they are at the trailing edge of the expandable intervertebral implant, such that insertion into the intervertebral space may be aided, although this is not a requirement and the expandable intervertebral implant may have a uniform thickness, when un-deployed, from the leading edge to the trailing edge. For similar reasons, the leading edge of the both the superior member and the inferior member may have a knifed or rounded shape. Once disposed in the intervertebral space, the expandable intervertebral implant is actuated and deployed, with the superior member and the inferior member moving apart from one another, seating against the associated intervertebral endplates, and distracting, realigning, and/or stabilizing them to a desired degree. In order to ensure that the expandable intervertebral implant is held securely in the intervertebral space, the external surface of each of the superior member and the inferior member is provided with a plurality of ridges or other friction structures, providing purchase with the associated intervertebral endplates.

When un-deployed, the superior member and the inferior member are configured such that they nest against one another, thereby providing the un-deployed expandable intervertebral implant with the smallest possible form factor for insertion through the skin and musculature of the patient and into the intervertebral space. In the exemplary embodiment provided, this is accomplished via the use of cut-away sections associated with the superior member and the inferior member, not unlike a tongue-in-groove joint assembly. The combined total height of the superior member and the inferior member when nested together in the undeployed state is less than the sum of the heights of the superior member and the inferior member individually. This is accomplished via a plurality of nesting ramp structures and/or other angled surfaces associated with the superior member and/or the inferior member that selectively cause distraction/separation of the superior member and the inferior member via interaction with a translating wedge structure. These various ramp structures are offset (i.e. staggered) in such a manner that the form factor of the expandable intervertebral implant is minimized when undeployed.

In one exemplary embodiment, the present invention provides an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member and the inferior member. The expansion mechanism includes a wedge structure that is translated between the superior member and the inferior member. The expansion mechanism also includes a screw that is coupled to the wedge structure and causes the wedge structure to translate when rotated. One or more of the superior member and the inferior member include a ramp structure on their opposed faces. Interaction of the wedge structure and the ramp structure of the one or more of the superior member and the inferior member as the wedge structure is translated causes adjustment of the separation of the superior member and the inferior member. The superior member is coupled to the inferior member through the wedge structure and the ramp structure of the one or more of the superior member and the inferior member. Optionally, the superior member is coupled to the inferior member via a track and rail system. The expansion mechanism disposed between the superior member and the inferior member may also be configured to selectively translate the superior member with respect to the inferior member.

In another exemplary embodiment, the present invention provides an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member and the inferior member, wherein the expansion mechanism includes a wedge structure that is translated between the superior member and the inferior member. The expansion mechanism also includes a screw that is coupled to the wedge structure and causes the wedge structure to translate when rotated. One or more of the superior member and the inferior member include a ramp structure on their opposed faces. Interaction of the wedge structure and the ramp structure of the one or more of the superior member and the inferior member as the wedge structure is translated causes adjustment of the separation of the superior member and the inferior member. The superior member is coupled to the inferior member through the wedge structure and the ramp structure of the one or more of the superior member and the inferior member. Optionally, the superior member is coupled to the inferior member via a track and rail system. The expansion mechanism disposed between the superior member and the inferior member may also be configured to selectively translate the superior member with respect to the inferior member.

In a further exemplary embodiment, the present invention provides a spinal surgical method, including: providing an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member and the inferior member; disposing the expandable intervertebral implant between the superior intervertebral body and the inferior intervertebral body; and selectively adjusting the separation of the superior member and the inferior member, thereby selectively adjusting a distraction of the superior intervertebral body from the inferior intervertebral body. The expansion mechanism includes a wedge structure that is translated between the superior member and the inferior member. The expansion mechanism also includes a screw that is coupled to the wedge structure and causes the wedge structure to translate when rotated. One or more of the superior member and the inferior member include a ramp structure on their opposed faces. Interaction of the wedge structure and the ramp structure of the one or more of the superior member and the inferior member as the wedge structure is translated causes adjustment of the separation of the superior member and the inferior member. The superior member is coupled to the inferior member through the wedge structure and the ramp structure of the one or more of the superior member and the inferior member. Optionally, the superior member is coupled to the inferior member via a track and rail system. The expansion mechanism disposed between the superior member and the inferior member may also be configured to selectively translate the superior member with respect to the inferior member.

BRIEF DESCRIPTION OF THE DRAWINGS

The expandable intervertebral implant of the present invention is illustrated and described herein with reference to the various drawings, in which like reference numbers are used to denote like device components, as appropriate, and in which.

DETAILED DESCRIPTION OF THE INVENTION

Figure 1:
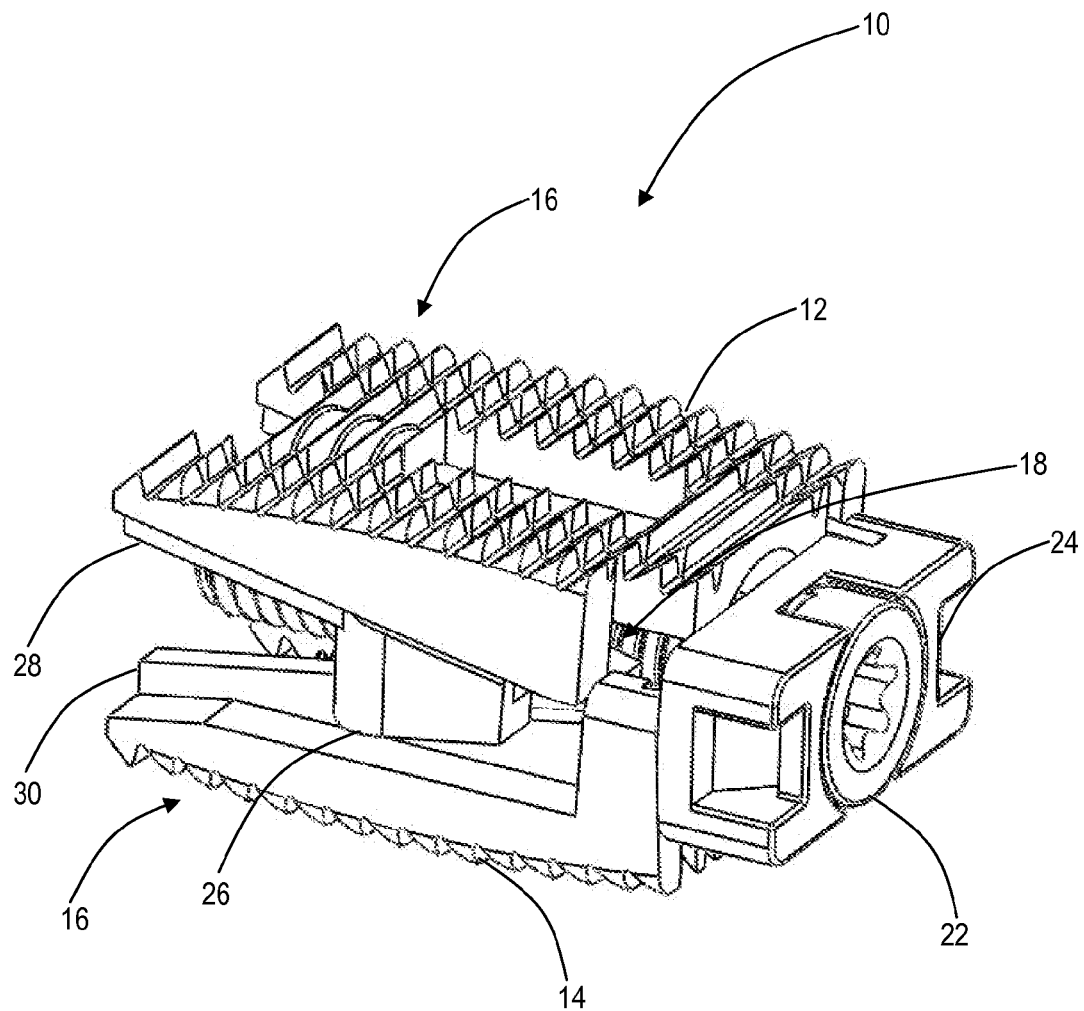
FIG. 1 is a perspective view of one exemplary embodiment of the expandable intervertebral implant of the present invention.

Referring to FIG. 1, in one exemplary embodiment, the present invention provides an expandable intervertebral implant 10 that is selectively disposed in the intervertebral space and deployed, thereby in-situ distracting, realigning, and/or stabilizing or fusing a portion of the spine of a patient in the treatment of injury, disease, and/or degenerative condition. The expandable intervertebral implant 10 includes a superior member 12 and an inferior member 14, each of which has a partially or substantially wedge or prismatic shape and a partially or substantially convex or other-shaped surface that is suitable for engaging the substantially concave surfaces of the associated bony superior and inferior intervertebral endplates. Optionally, the superior member 12 and the inferior member 14 are each thinner at the leading edge of the expandable intervertebral implant 10 than they are at the trailing edge of the expandable intervertebral implant 10, such that insertion into the intervertebral space may be aided, although this is not a requirement and the expandable intervertebral implant 10 may have a uniform thickness, when un-deployed, from the leading edge to the trailing edge. For similar reasons, the leading edge of the both the superior member 12 and the inferior member 14 may have a knifed or rounded shape. Once disposed in the intervertebral space, the expandable intervertebral implant 10 is actuated and deployed, with the superior member 12 and the inferior member 14 moving apart from one another, seating against the associated intervertebral endplates, and distracting, realigning, and/or stabilizing them to a desired degree. The mechanisms by which this happens are described in greater detail herein below. This operation is analogous to placing a jack under a car, positioning it appropriately, snugging it in the space beneath the car, and then jacking it up. In order to ensure that the expandable intervertebral implant 10 is held securely in the intervertebral space, the external surface of each of the superior member 12 and the inferior member 14 is provided with a plurality of ridges 16 or other friction structures, providing purchase with the associated intervertebral endplates. The overall dimensions of the expandable intervertebral implant 10 are on the order of several millimeters to tens of millimeters, such that 5-20 mm of expansion are provided, for example.

When un-deployed, the superior member 12 and the inferior member 14 are configured such that they nest against one another, thereby providing the un-deployed expandable intervertebral implant 10 with the smallest possible form factor for insertion through the skin and musculature of the patient and into the intervertebral space. In the exemplary embodiment illustrated in FIG. 1, this is accomplished via the use of cut-away sections 18 and 20 associated with the superior member 12 and the inferior member 14.

By way of overview, the superior member 12 and the inferior member 14 are actuated via the rotation of a screw 22 disposed through a housing 24 located at the training edge of the expandable intervertebral implant 10. This screw 22 is disposed along the central axis of the expandable intervertebral implant 10, between the superior member 12 and the inferior member 14. The screw 22 engages an internally-threaded wedge structure 26 disposed between the superior member 12 and the inferior member 14, selectively translating the wedge structure 26 along the central axis of the expandable intervertebral implant 10 with rotation. This translation causes the wedge structure 26 to interact with an associated wedge shape or structure of the superior member 12 and/or inferior member 14, thereby forcing the superior member 12 and the inferior member 14 apart/together with translation of the wedge structure 26. Preferably, the superior member 12 and the inferior member 14 each include a track structure 28 and 30, thereby securely coupling the superior member 12 to the inferior member 14 through the wedge structure 26. The interaction of the wedge structure 26 with the wedge shape or structure of the superior member 12 and/or inferior member 14 during translation preferably causes the superior member 12 and the inferior member 14 to move apart/together while maintaining a substantially parallel relationship. Alternatively, the superior member 12 and the inferior member 14 may move apart with a predetermined lordotic angle. The superior member 12 and the inferior member 14 may move apart in a substantially-continuous fashion, or they may move apart in 0.5-mm increments, for example. In addition, the interaction of the wedge structure 26, the superior member 12, and the inferior member 14 may be designed such that as the superior member 12 and the inferior member 14 move apart, they also translate with respect to one another. This is helpful in, for example, ensuring that the plurality of ridges 16 or other friction structures are securely seated in the bony material.

Figure 2:
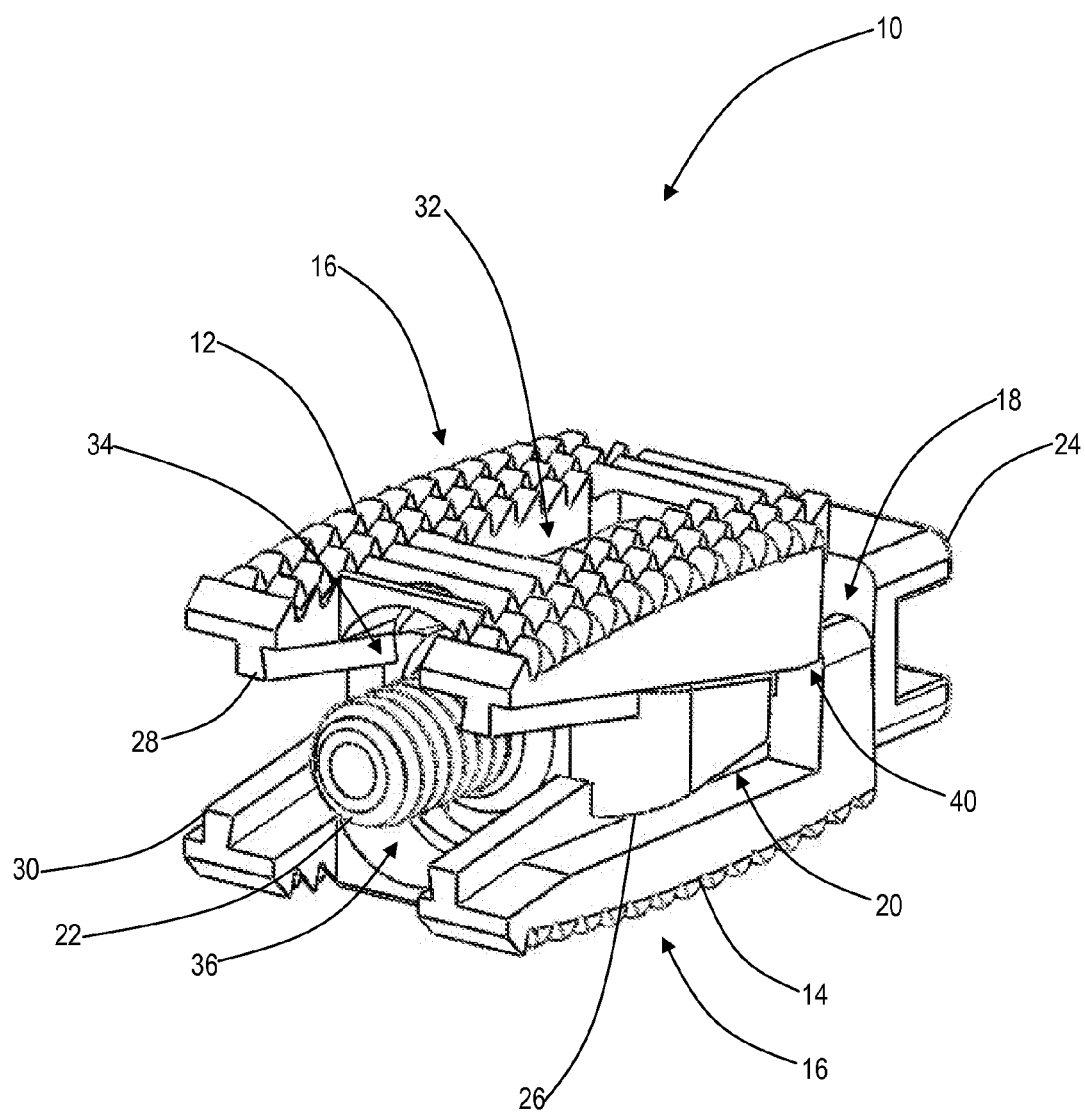
FIG. 2 is another perspective view of one exemplary embodiment of the expandable intervertebral implant of the present invention.
Figure 3:
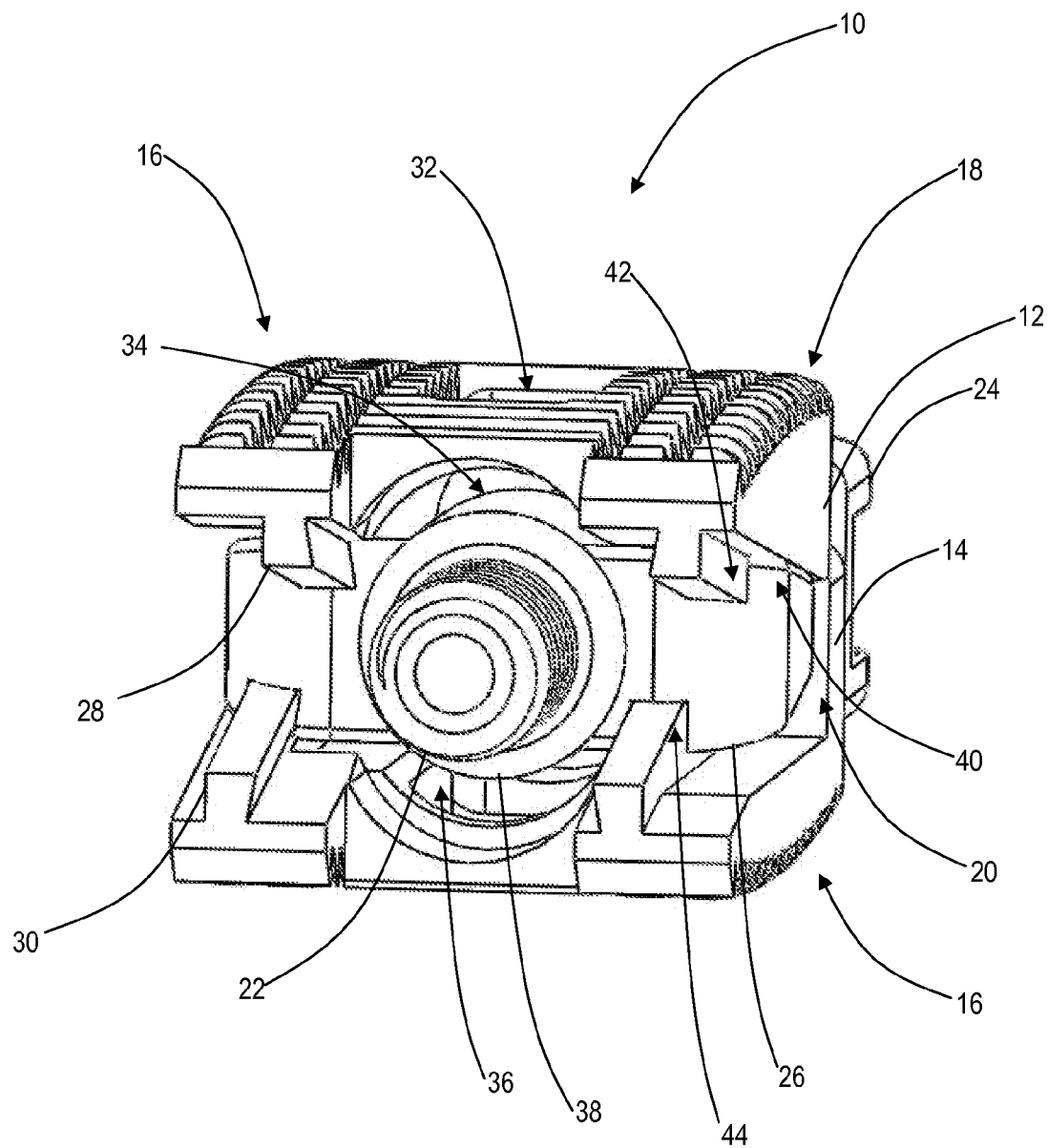
FIG. 3 is a further perspective view of one exemplary embodiment of the expandable intervertebral implant of the present invention.

Another view of the expandable intervertebral implant 10 is provided in FIGS. 2 and 3. As is evident from FIGS. 2 and 3, the superior member 12 and the inferior member 14 may each include one or more holes 32 or fenestrations to promote bony in-growth and fusion, as appropriate. Preferably, the superior member 12 and the inferior member 14 each include a groove 34 and 36 in which the screw 22 is disposed. This nesting of the screw 22 within the superior member 12 and the inferior member 14 provides the expandable intervertebral implant 10 with the smallest possible form factor when un-deployed, allowing the superior member 12 and the inferior member 14 to collapse together, without interference from the screw 22. The wedge structure 26 has a corresponding bore portion 38 (FIG. 3), through which the screw 22 passes and which sits within the grooves 34 and 36 of the superior member 12 and the inferior member 14, respectively. This configuration permits the wedge structure 26 to translate smoothly along the central axis of the expandable intervertebral implant 10 with rotation of the screw 22, distracting the superior member 12 and the inferior member 14, which holding the entire assembly in secure alignment. Along these same lines, the cut-away sections 18 and 20 of the superior member 12 and the inferior member 14, respectively, may form abutting surfaces 40 perpendicular to the central axis of the expandable intervertebral implant 10 that aide in holding the superior member 12 and the inferior member 14 in alignment, despite their degree of deployment, by resisting rotation of the superior member 12 and the inferior member 14 with respect to one another. Thus, the expandable intervertebral implant 10 will expand upon deployment, as opposed to "clamshelling." Also along these same lines, the track structures 28 and 30 of the superior member 12 and the inferior member 14 are "dove-tailed" on one or both sides and engage corresponding channels 42 and 44 manufactured into the superior and inferior surfaces of the wedge structure 26, again thereby securely coupling the superior member 12 to the inferior member 14 through the wedge structure 26.

Figure 4:
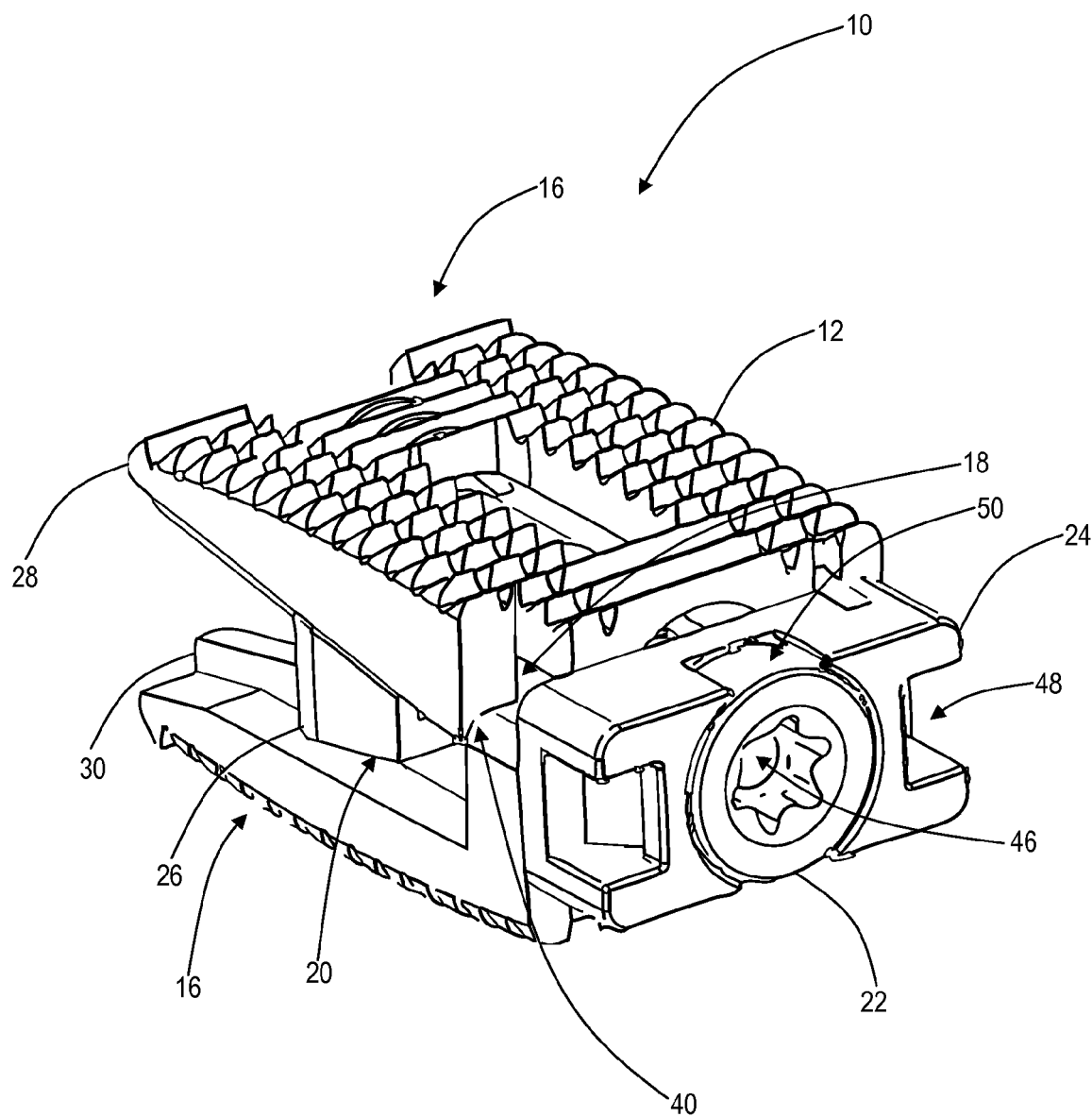
FIG. 4 is a still further perspective view of one exemplary embodiment of the expandable intervertebral implant of the present invention.

Referring to FIG. 4, the screw 22 preferably includes a keyed recess 46 for receiving a driver, such as a hexalobular driver, by which the screw 22 is rotated to translate the wedge structure 26. The housing 24 includes a plurality of recesses 48 or the like for receiving a holding/placement tool. As is described in greater detail herein below, the driver and holding/placement tool may be incorporated into one assembly, such that the expandable intervertebral implant 10 may be grasped, positioned, expanded, and released in a series of simple steps, by a single surgeon, using a single tool. As is also illustrated in FIG. 4, the housing 24 may include a cylindrical recess 50 that is configured to substantially contain the head of the screw 22, again reducing the overall footprint of the expandable intervertebral implant 10.

Figure 5:
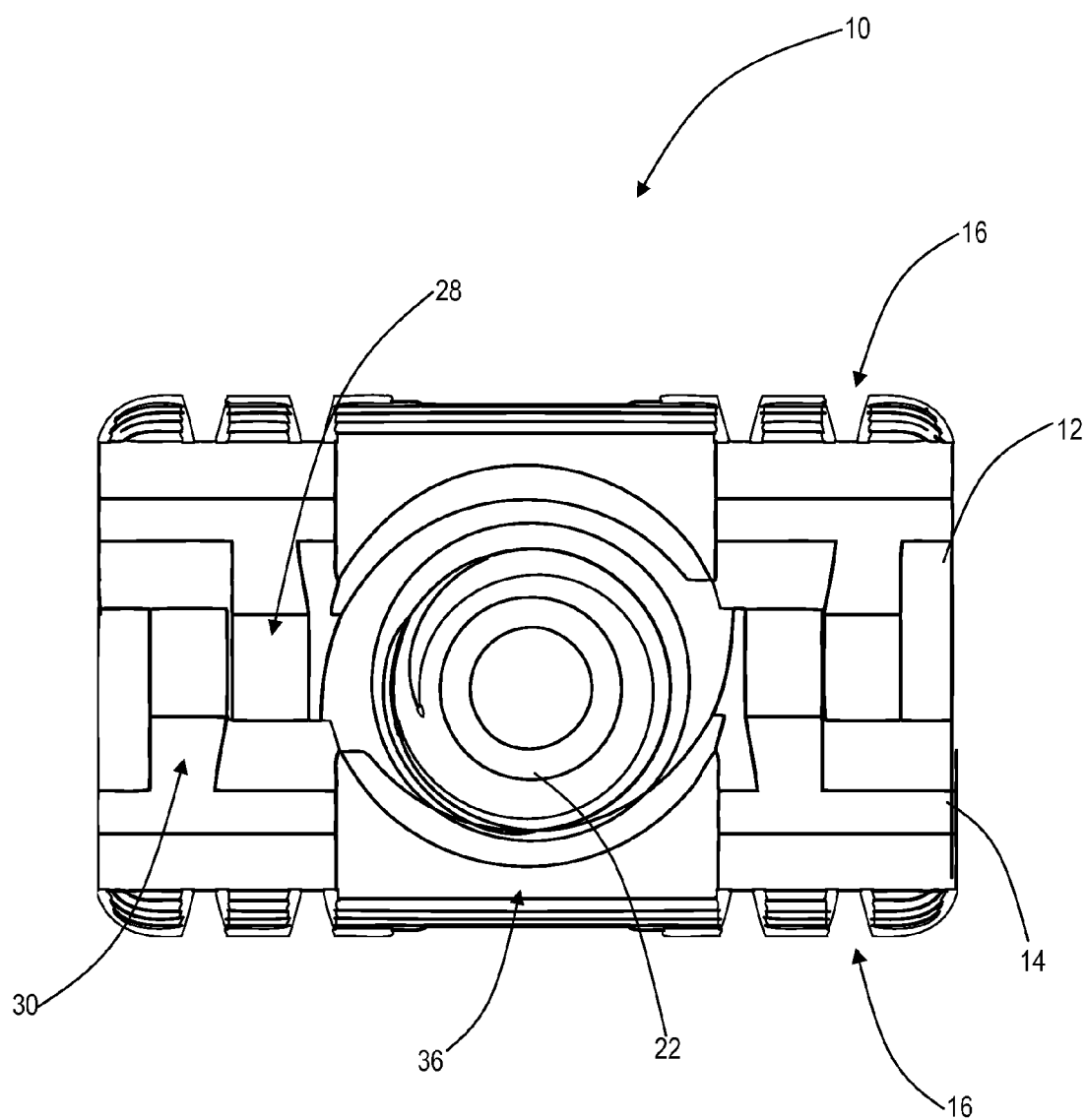
FIG. 5 is a planar end view of one exemplary embodiment of the expandable intervertebral implant of the present invention.
Figure 6:
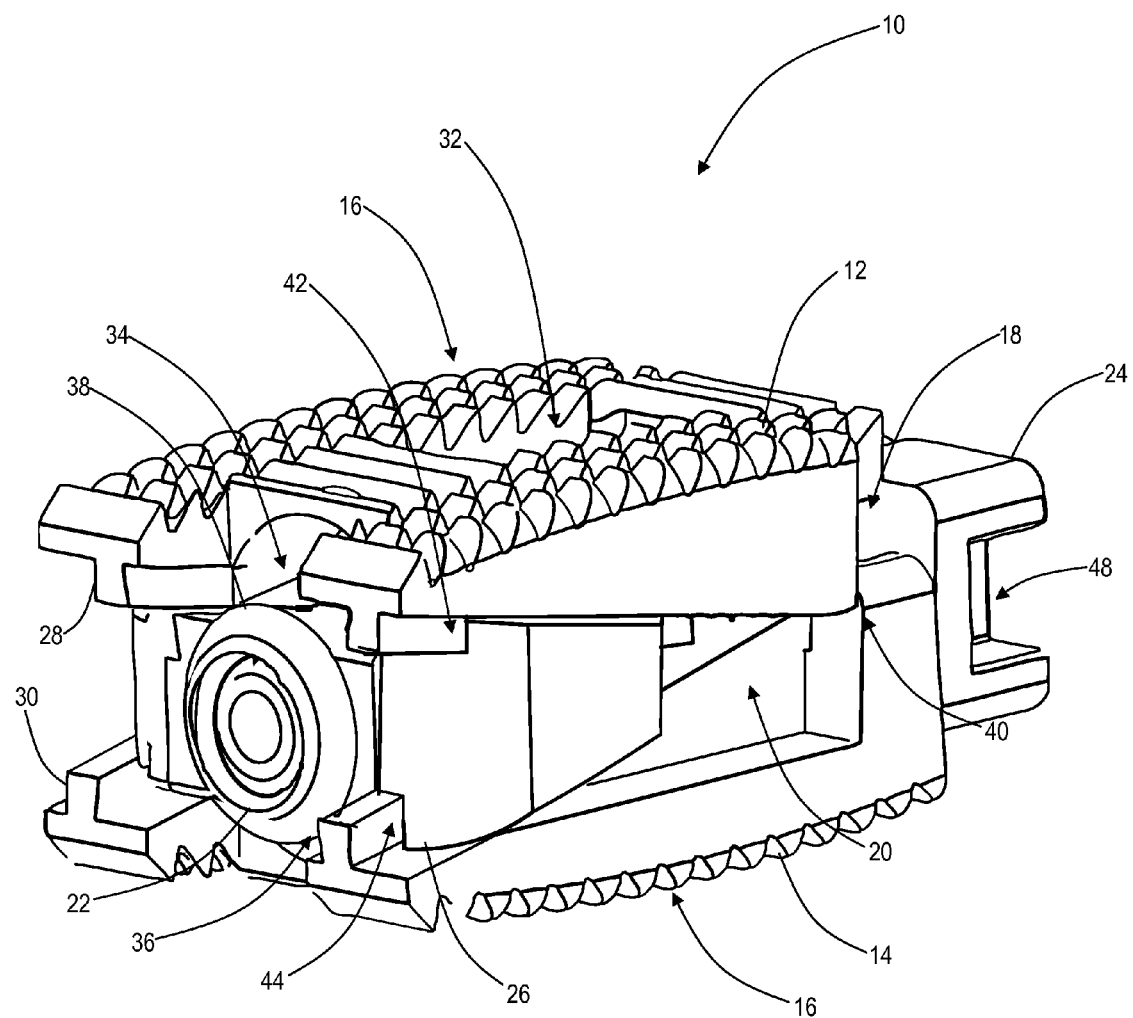
FIG. 6 is a still further perspective view of one exemplary embodiment of the expandable intervertebral implant of the present invention.
Figure 7:
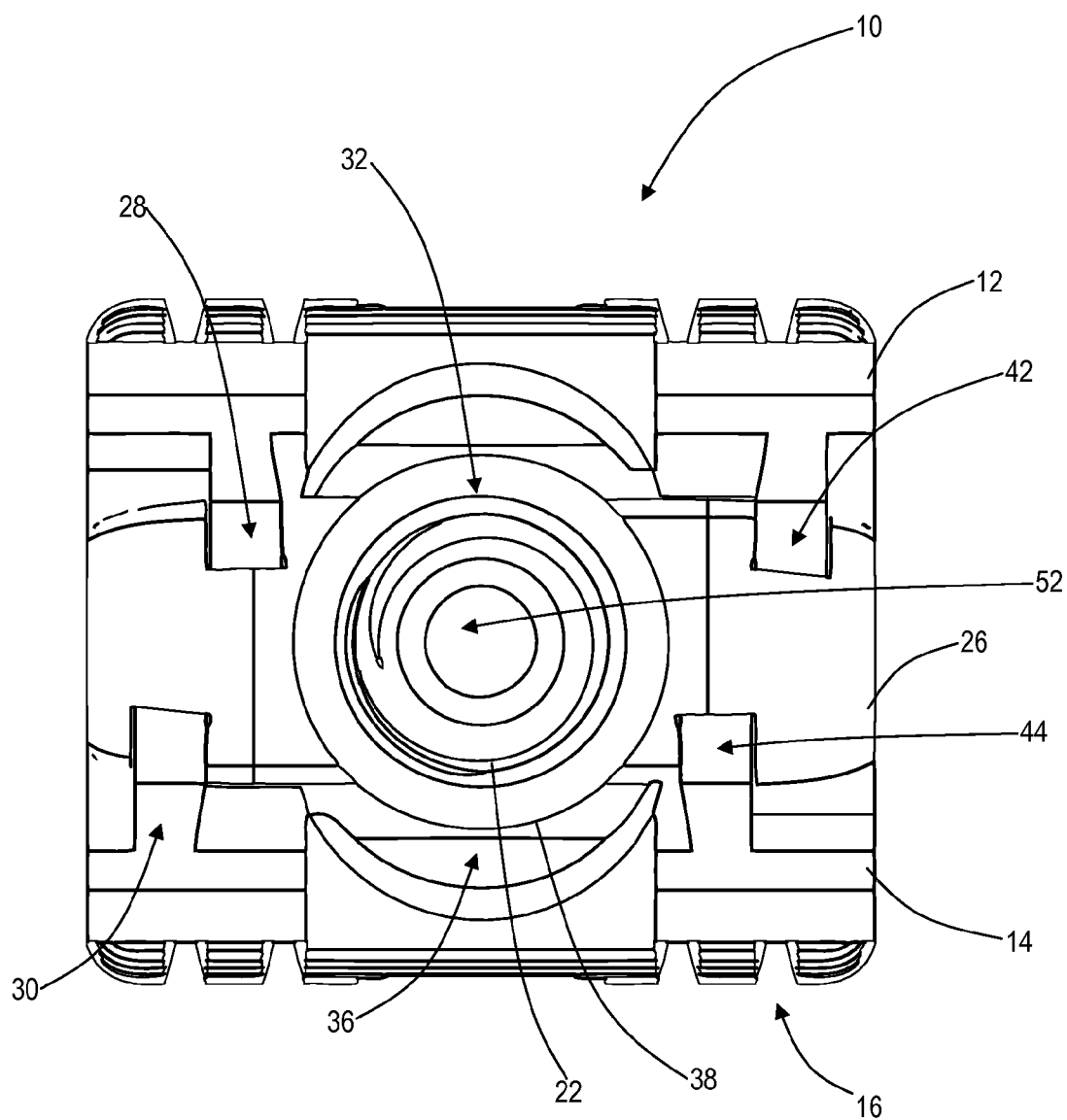
FIG. 7 is another planar end view of one exemplary embodiment of the expandable intervertebral implant of the present invention.

FIG. 5 illustrates the cross-sectional footprint of the expandable intervertebral implant 10 along its central axis, demonstrating how the superior member 12 and the inferior member 14 nest with one another about the screw 22 during implantation. FIG. 6 illustrates the expandable intervertebral implant 10 in an only partially-deployed state, while FIG. 7 illustrates the cross-sectional footprint of the expandable intervertebral implant 10 along its central axis, demonstrating how the superior member 12 and the inferior member 14 expand away from one another about the screw 22 and wedge structure 26 during actuation and deployment. As is illustrated clearly in FIGS. 5 and 7, the screw 22 may be cannulated, and a have a bore 52 passing through it along the central axis of the expandable intervertebral implant 10. This cannulation aides in the placement of the expandable intervertebral implant 10 over a guide-wire or the like.

Figure 8:
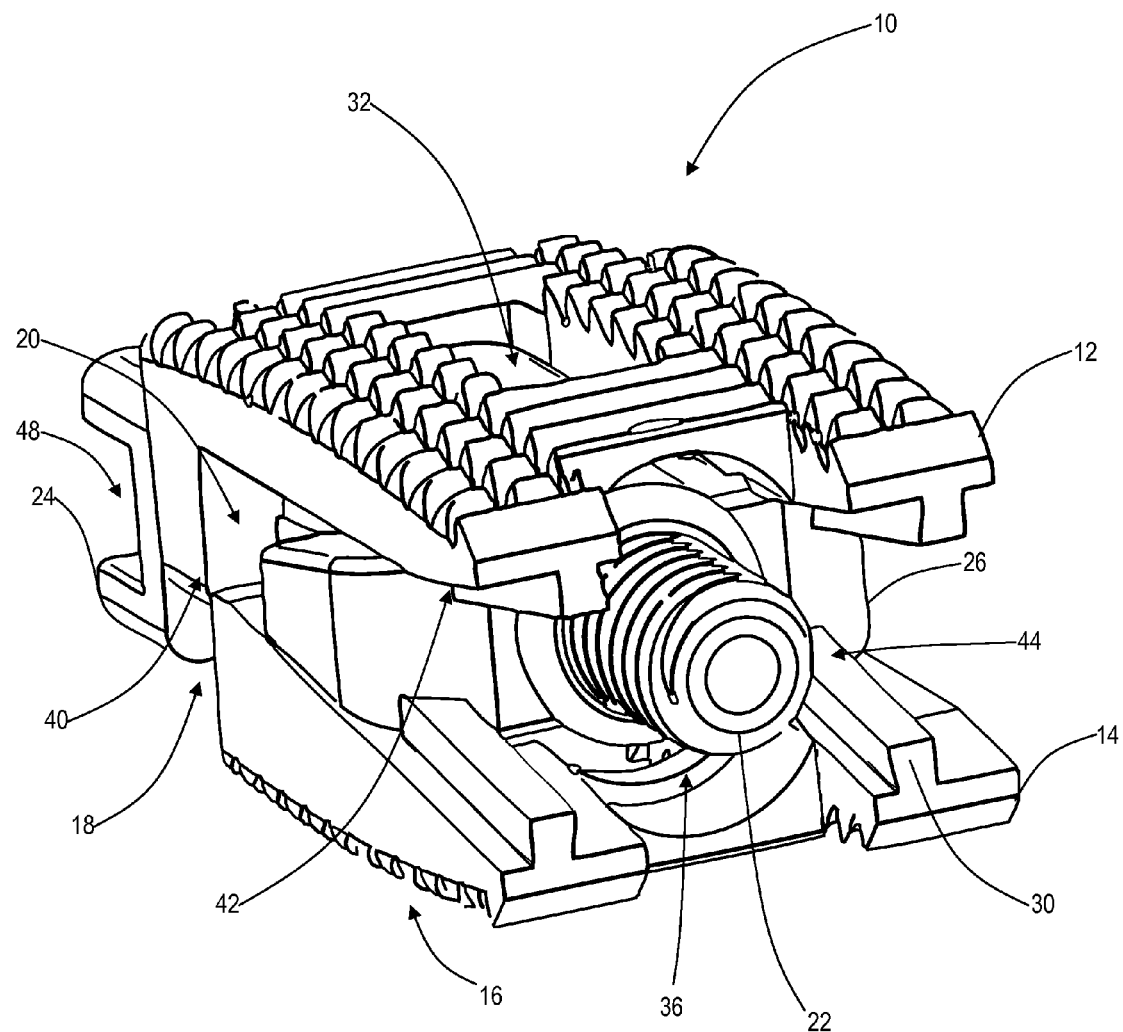
FIG. 8 is a still further perspective view of one exemplary embodiment of the expandable intervertebral implant of the present invention.

Referring to FIG. 8, it may be seen that the track structures 28 and 30 of the superior member 12 and the inferior member 14, respectively, are offset from one another relative to the central axis of the expandable intervertebral implant 10 such that they sit side-by-side when the expandable intervertebral implant 10 is un-depolyed, thereby making the assembly as compact as possible. Accordingly, the channels 42 and 44 manufactured into the superior and inferior surfaces of the wedge structure 26, respectively, are also offset from one another relative to the central axis of the expandable intervertebral implant 10. FIG. 8 also illustrates the interaction of the slopes of the wedge structure 26 and, in this exemplary embodiment, the superior member 12. Again, the interaction of the wedge structure 26 with the wedge shape or structure of the superior member 12 and/or inferior member 14 during translation preferably causes the superior member 12 and the inferior member 14 to move apart/together while maintaining a substantially parallel relationship.

Figure 9A:
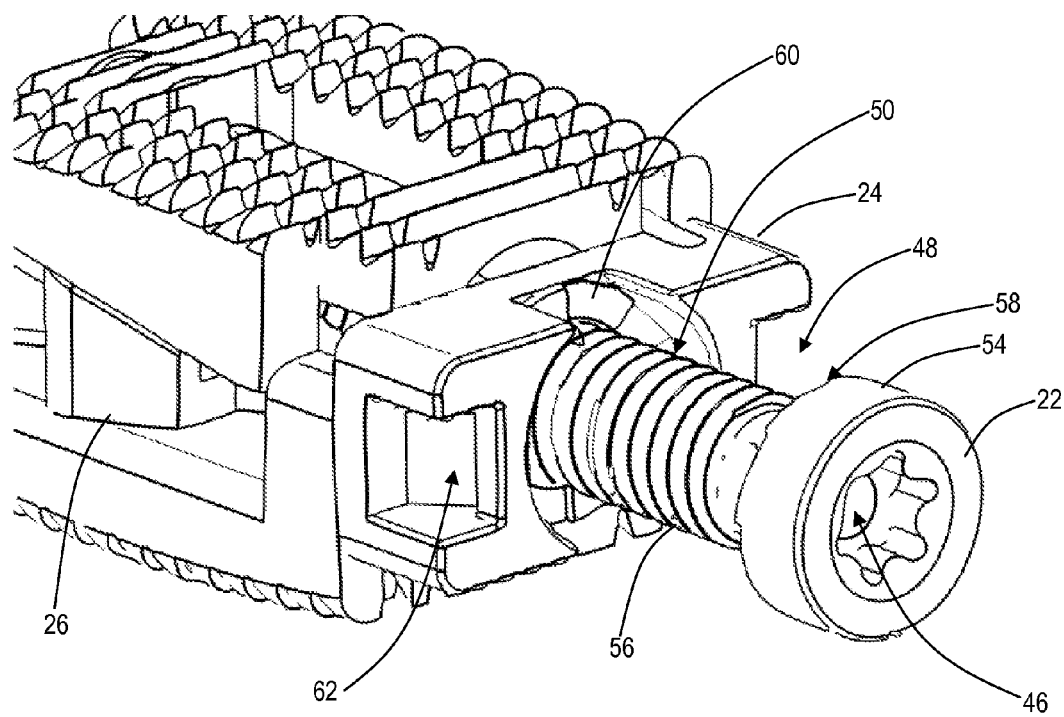
FIG. 9a is a partial perspective view of one exemplary embodiment of the expandable intervertebral implant of the present invention.
Figure 9B:
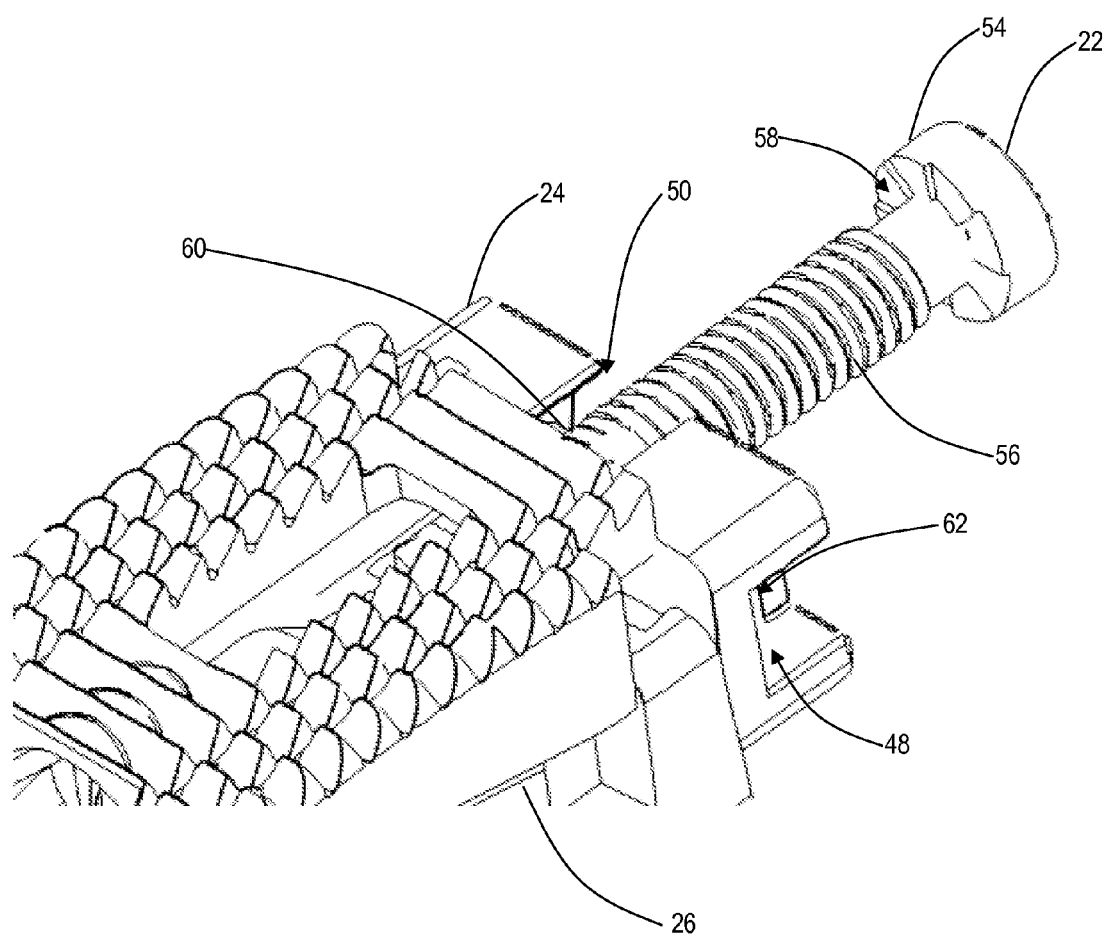
FIG. 9b is another partial perspective view of one exemplary embodiment of the expandable intervertebral implant of the present invention.
Figure 10A:
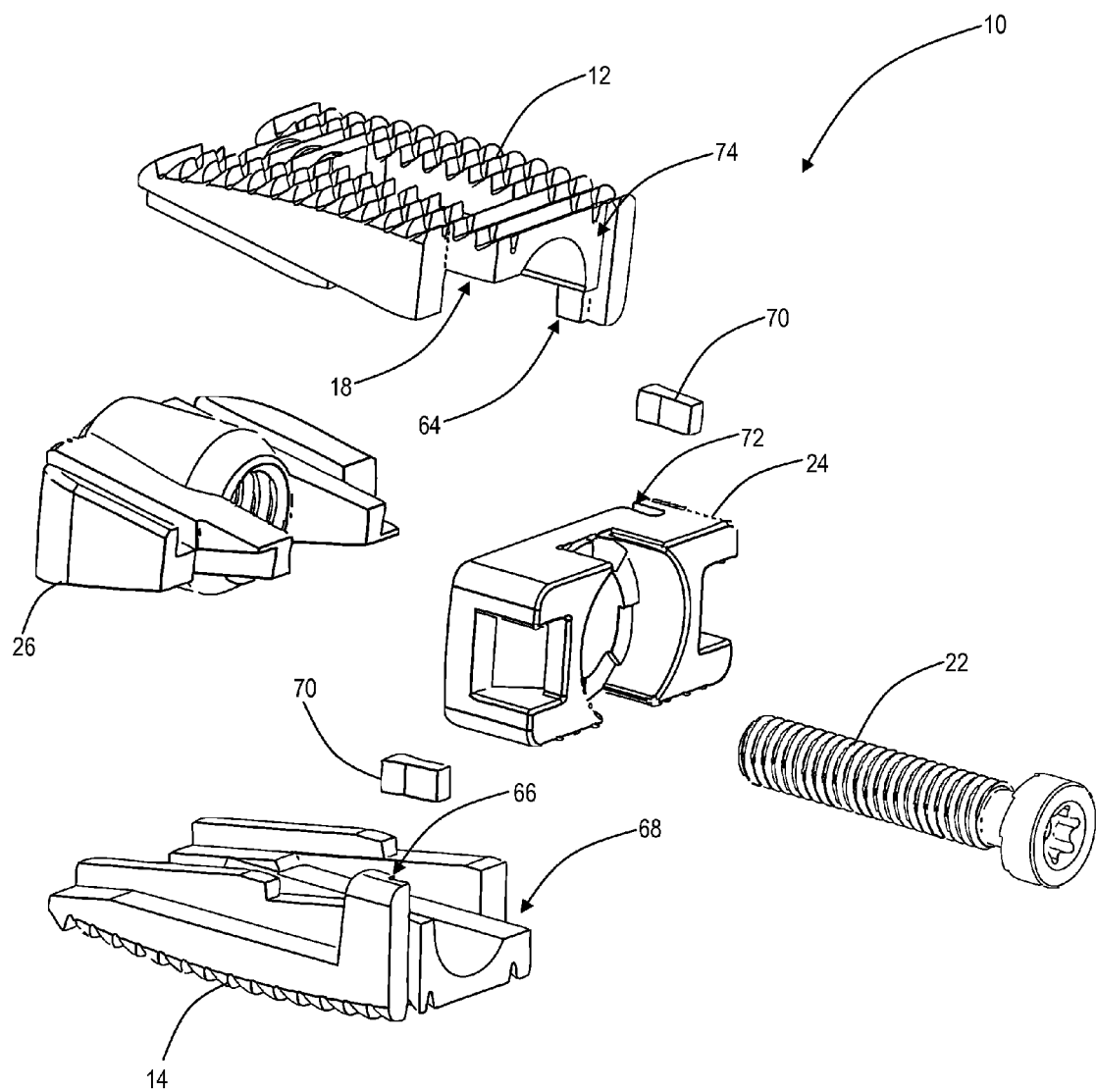
FIG. 10a is an exploded perspective view of one exemplary embodiment of the expandable intervertebral implant of the present invention.
Figure 10B:
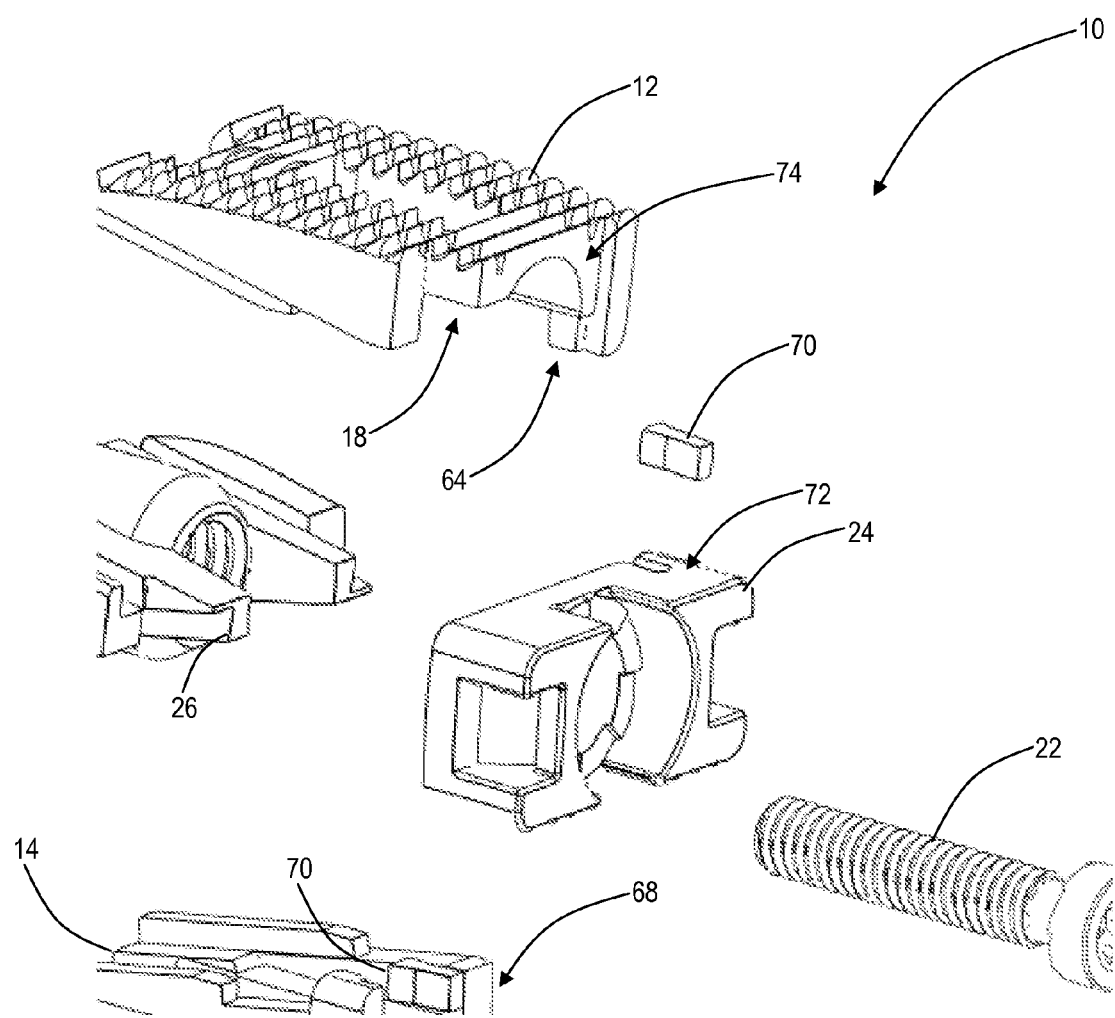
FIG. 10b is a partial exploded perspective view of one exemplary embodiment of the expandable intervertebral implant of the present invention.
Figure 10C:
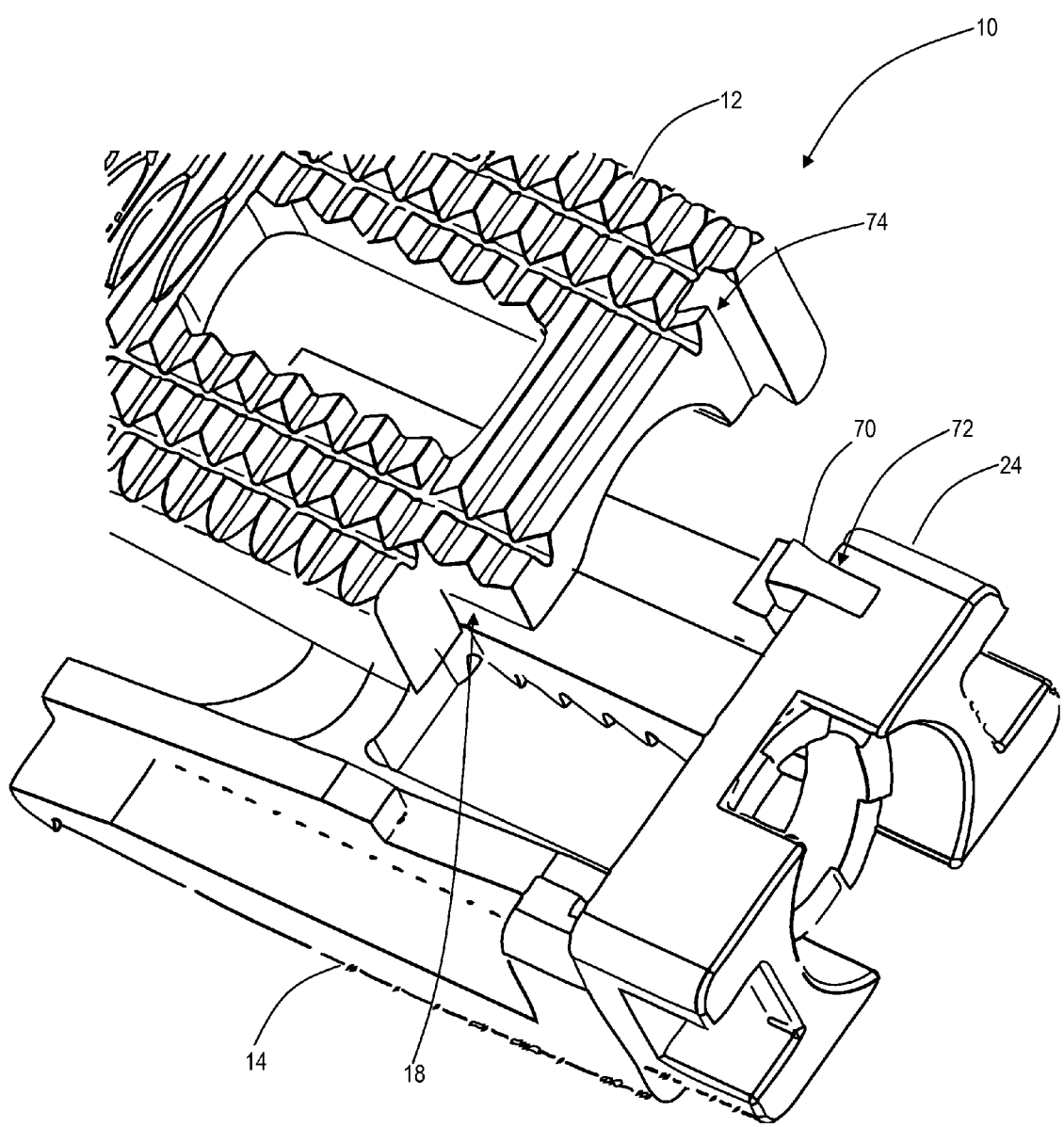
FIG. 10c is another partial exploded perspective view of one exemplary embodiment of the expandable intervertebral implant of the present invention.
Figure 10D:
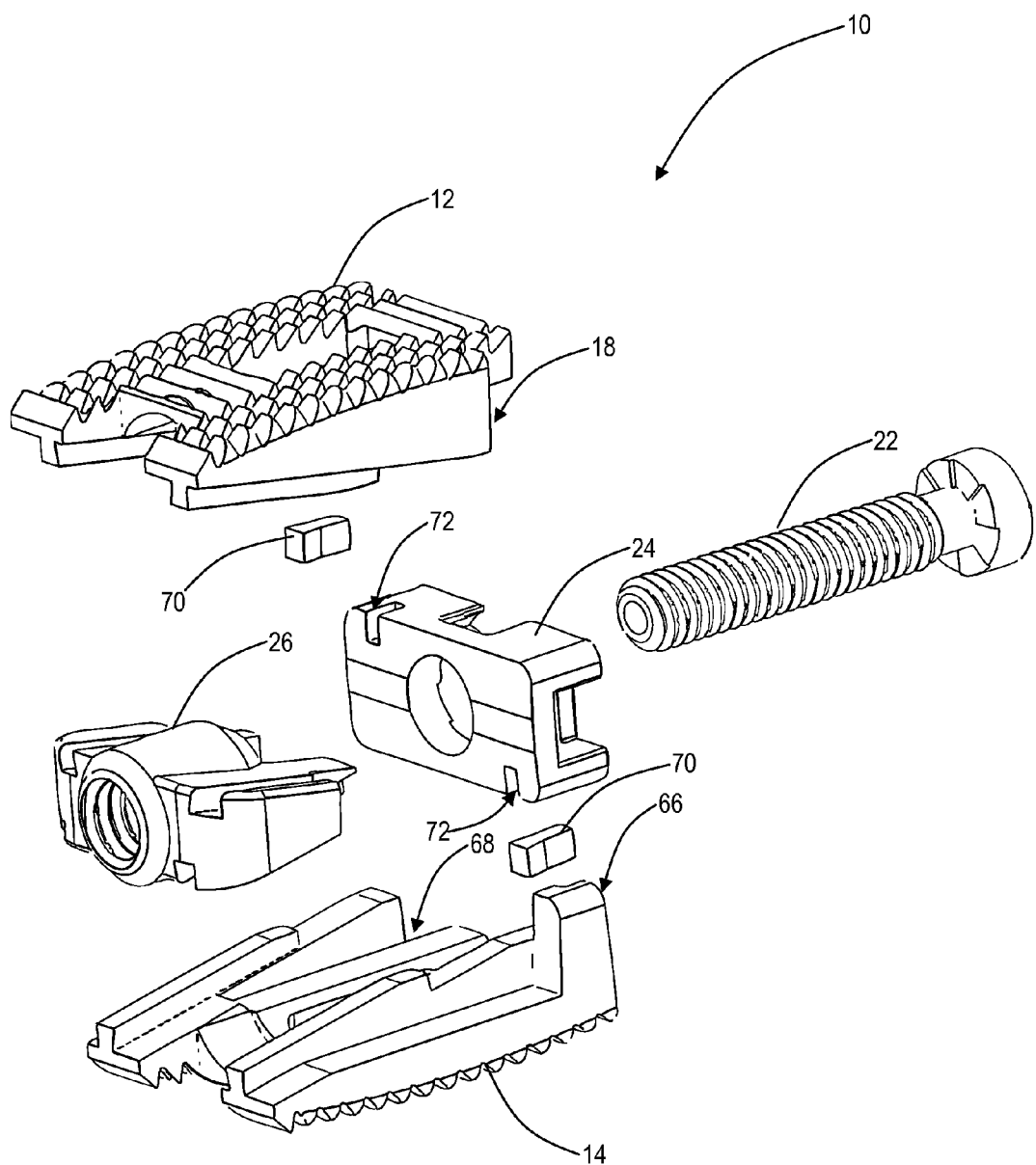
FIG. 10d is another exploded perspective view of one exemplary embodiment of the expandable intervertebral implant of the present invention.
Figure 10E:
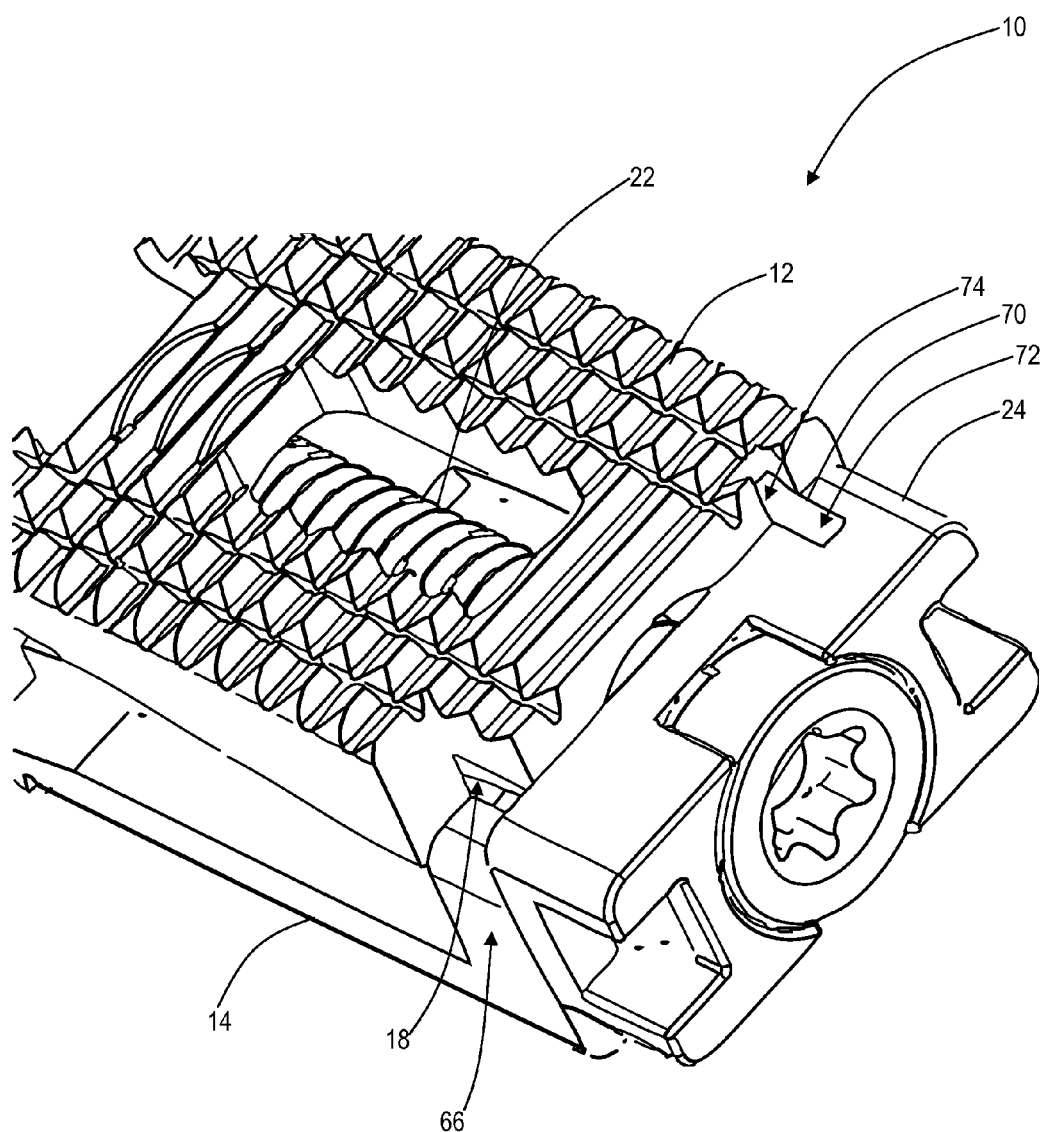
FIG. 10e is a further partial exploded perspective view of one exemplary embodiment of the expandable intervertebral implant of the present invention.

Referring to FIGS. 9a and 9b, the screw 22 includes a head portion 54 that selectively sits within the cylindrical recess 50 of the housing 24 and a threaded portion 56 that passes through the housing 24 to engage the wedge structure 26. When properly positioned, the head portion 54 of the screw 22 sits flush with the exterior surface of the expandable intervertebral implant 10 and does not protrude. Preferably, the back side of the head portion 54 of the screw 22 includes a plurality of teeth 58 or the like that frictionally engage the screw 22 with a corresponding plurality of teeth 60 or the like manufactured into the exposed floor of the cylindrical recess 50 of the housing 24. This ratcheting or spiral jaw clutch mechanism aides in preventing unwanted rotation of the screw 22 and corresponding translation of the wedge structure 26. This may also aide in allowing the screw 22 to be rotated in a ratcheting or step-wise manner, with specific detent points. It should be noted that a lock-washer or the like could also be used for this purpose, and that a non-screw-based translation assembly could be used to translate and secure the wedge structure 26, as will be readily apparent to those of ordinary skill in the art. Each of the plurality of holding/placement tool recesses 48 includes a lip structure 62 that is selectively engaged by a corresponding hook structure of the tool.

Referring to FIGS. 10a-10e, the superior member 12 and the inferior member include opposing flanges 64 and 66 that fit within the corresponding cut-away sections 68 and 18 of the inferior member 14 and the superior member 12, respectively, when the superior member 12 and the inferior member 14 are nested against one another and/or separated by a predetermined distance. These opposing flanges 64 and 66 aide in providing stability to the expandable intervertebral implant 10 by preventing the superior member 12 and the inferior member 14 from sliding with respect to one another and the central axis of the expandable intervertebral implant 10. These figures illustrate that the superior member 12 and the inferior member 14 are coupled to one another, but allowed to expand away from/contract towards one another, via a pair of "dove-tailed" inserts 70 or the like disposed on either side of the expandable intervertebral implant 10 that engage both a channel 72 manufactured into the housing 24 and a channel 74 manufactured into the superior member 12 and the inferior member 14. It will be readily apparent to those of ordinary skill in the art that other suitable coupling mechanisms may also be used. In the exemplary embodiment illustrated, only the portion of the inserts 70 engaging the superior member 12 and the inferior member 14 is "dove-tailed," while the portion engaging the housing 24 is not.

Figure 11:
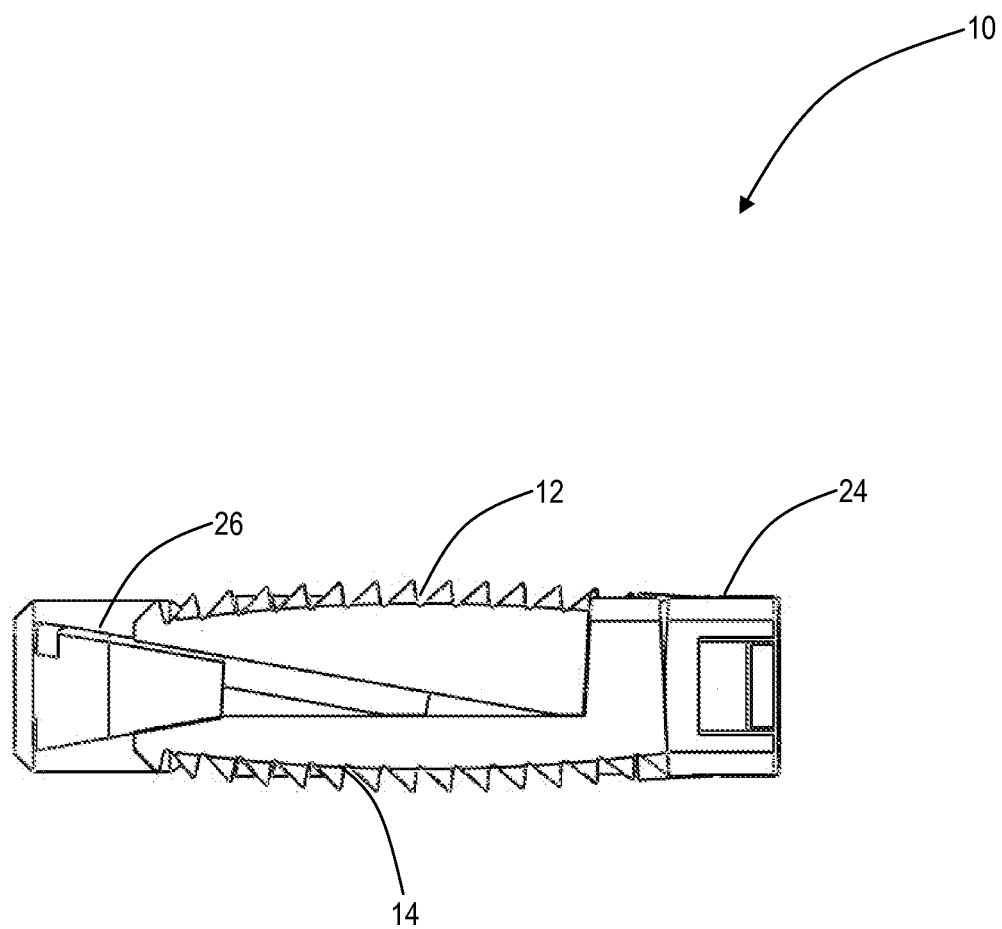
FIG. 11 is a planar side view of one exemplary embodiment of the expandable intervertebral implant of the present invention.
Figure 12:
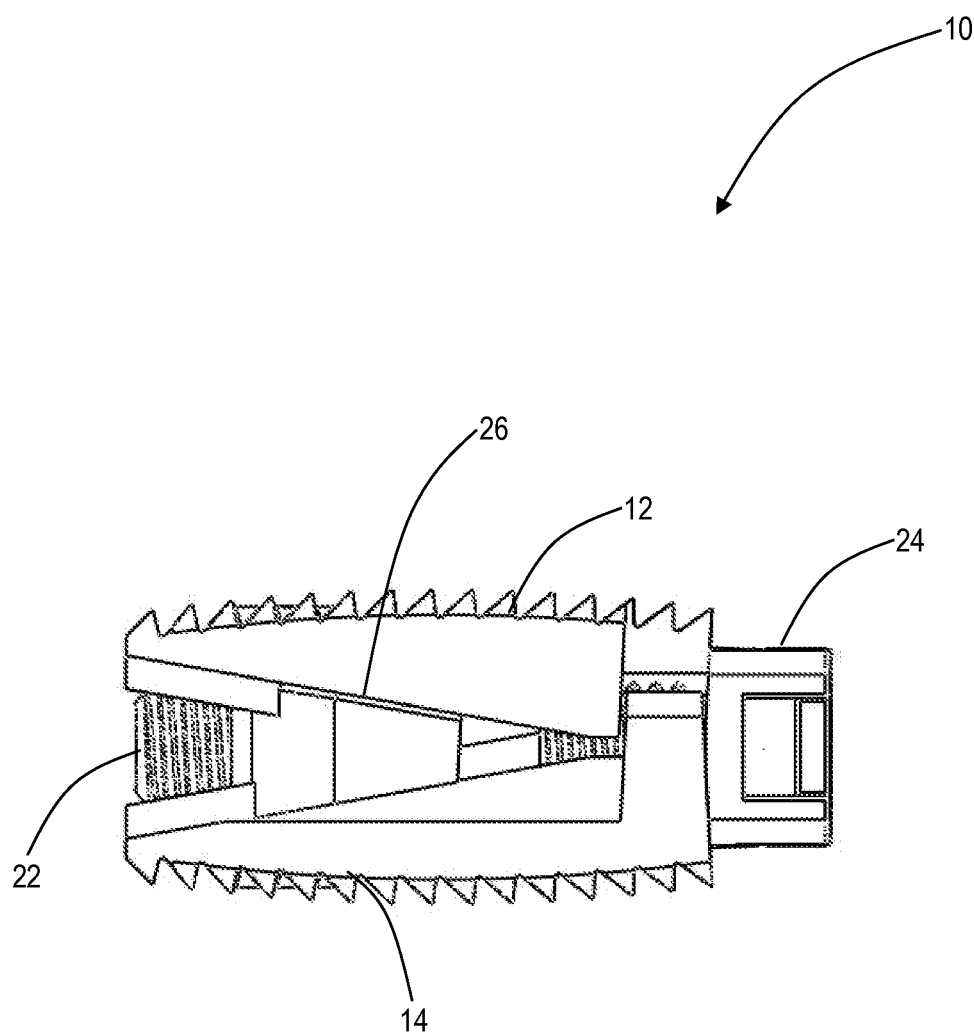
FIG. 12 is another planar side view of one exemplary embodiment of the expandable intervertebral implant of the present invention.
Figure 13:
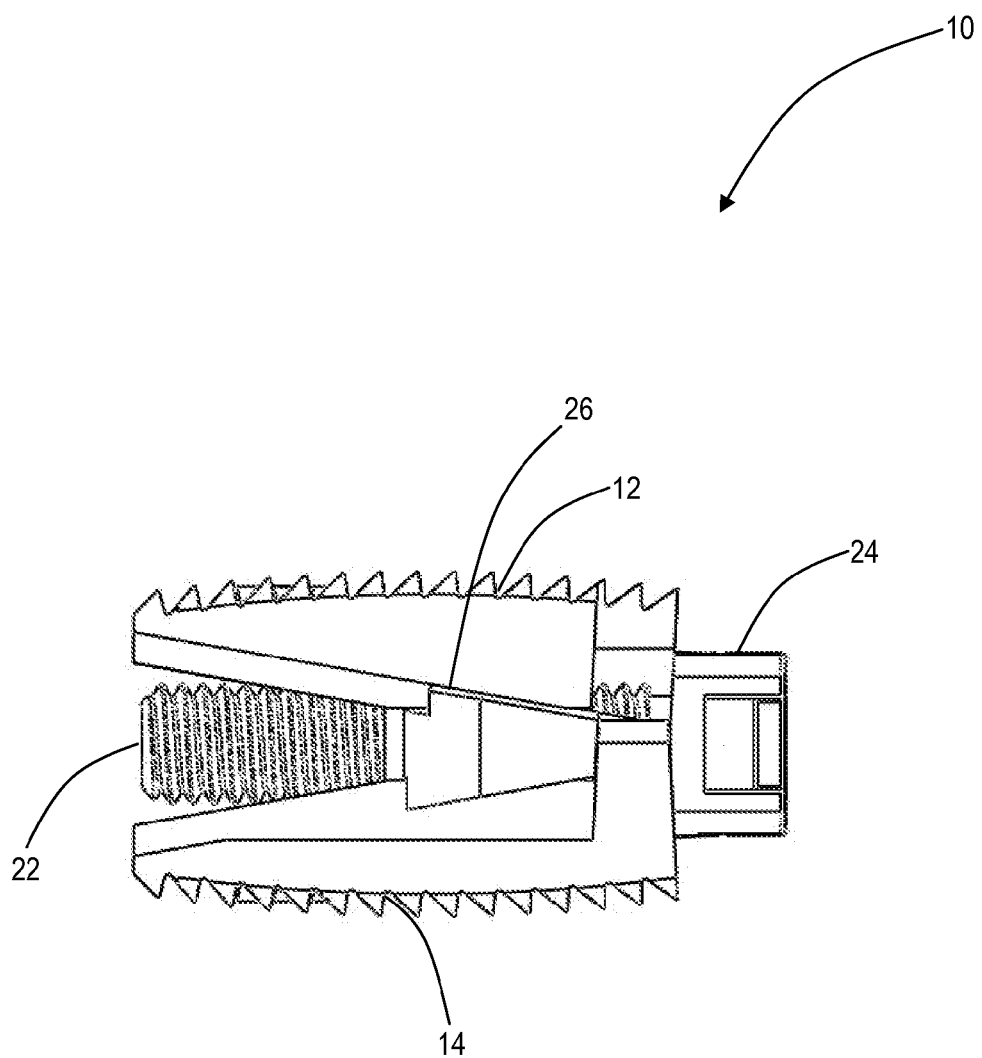
FIG. 13 is a further planar side view of one exemplary embodiment of the expandable intervertebral implant of the present invention.

FIGS. 11-13 illustrate the "opening" of the expandable intervertebral implant 10 via rotation of the screw 22 and translation of the wedge structure 26 towards the housing 24. The constant, substantially-parallel relationship of the superior member 12 and the inferior member 14 should be noted as the wedge structure 26 move along the "rails" of the superior member 12 and the inferior member 14.

Figure 14:
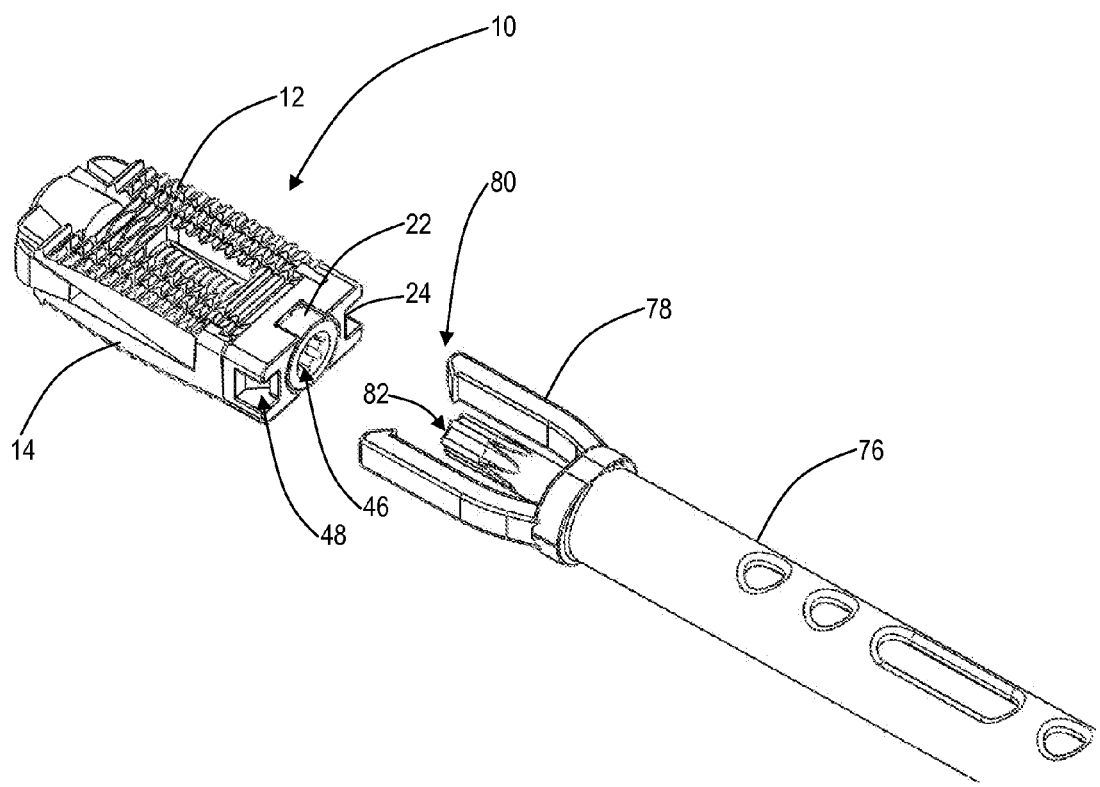
FIG. 14 is a still further perspective view of one exemplary embodiment of the expandable intervertebral implant of the present invention, along with a partial perspective view of one exemplary embodiment of the implantation tool of the present invention.
Figure 15:
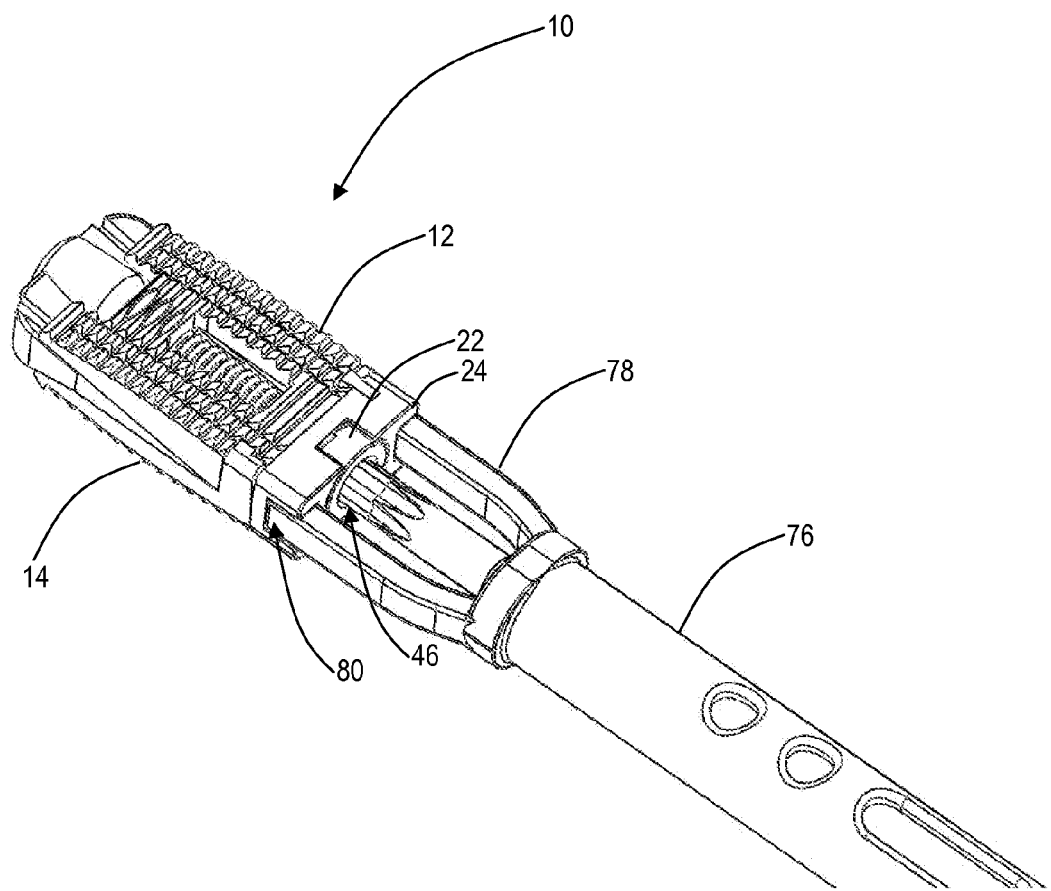
FIG. 15 is a still further perspective view of one exemplary embodiment of the expandable intervertebral implant of the present invention, along with another partial perspective view of one exemplary embodiment of the implantation tool of the present invention.

Referring to FIGS. 14 and 15, in one exemplary embodiment, the combination placement/deployment tool 76 of the present invention includes a pair of elongate arms 78 that each have a hook structure 80 on the end that is configured to selectively and releasably engage the corresponding recess 48 of the housing 24. The combination placement/deployment tool 76 also includes a driver 82 disposed between the pair of elongate arms 78 that is configured to selectively and releasably engage the keyed recess 46 of the screw 22. When rotated, the driver 82 rotates the screw 22, thereby translating the wedge structure 26 (not illustrated) and expanding/contracting the superior member 12 and the inferior members 14 of the expandable intervertebral implant.

Figure 16:
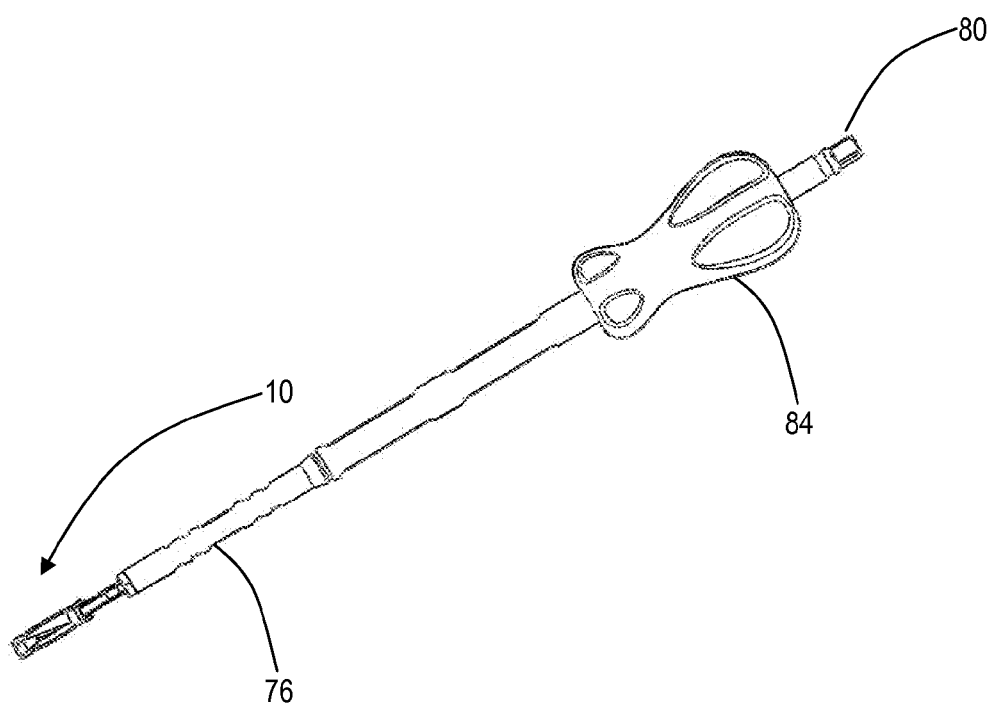
FIG. 16 is a still further perspective view of one exemplary embodiment of the expandable intervertebral implant of the present invention, along with a perspective view of one exemplary embodiment of the implantation tool of the present invention.
Figure 17:
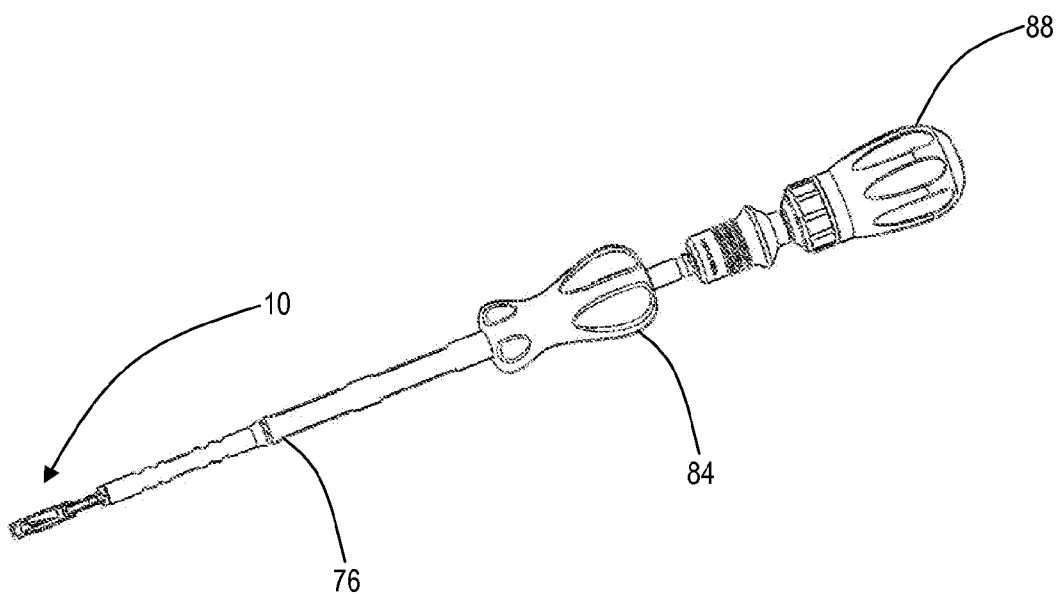
FIG. 17 is a still further perspective view of one exemplary embodiment of the expandable intervertebral implant of the present invention, along with another perspective view of one exemplary embodiment of the implantation tool of the present invention.

Referring to FIGS. 16 and 17, the combination placement/deployment tool 76 further includes a handle 84 for grasping and a socket 86 for attaching a rotating or driver handle 88, such as a ratcheting handle. It will be readily apparent to those of ordinary skill in the art that the expandable intervertebral implant of the present invention may be placed via an open surgical procedure, or via any suitable minimally-invasive portal-type of system.

Although the expandable intervertebral implant of the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples fall within the spirit and scope of the present invention, are contemplated herein, and are intended to be covered by the following claims.

What is claimed is:

1. An expandable intervertebral implant, comprising:
a superior member configured to engage a superior intervertebral body;
an inferior member configured to engage an inferior intervertebral body; and
an expansion mechanism disposed between the superior member and the inferior member configured to selectively adjust a vertical separation of the superior member and the inferior member, wherein the expansion mechanism comprises a wedge structure that is translated between the superior member and the inferior member;
wherein the superior member is coupled to the inferior member through the wedge structure via a track and rail system, wherein the superior member and the inferior member each comprise a pair of rails, wherein the rails of the superior member are horizontally offset relative to the rails of the inferior member such that each rail of the superior member is disposed substantially side-by-side horizontally adjacent to a respective one of the rails of the inferior member when the expandable vertebral implant is in an unexpanded configuration, and wherein one rail of the superior member is disposed between an associated rail of the inferior member and a central axis of the implant and another rail of the inferior member is disposed between the associated rail of the superior member and the central axis of the implant in the unexpanded configuration.

2. The expandable intervertebral implant of claim 1, wherein the expansion mechanism further comprises a screw that is coupled to the wedge structure and causes the wedge structure to translate when rotated.

3. The expandable intervertebral implant of claim 1, wherein one or more of the superior member and the inferior member comprise a ramp structure on their opposed faces.

4. The expandable intervertebral implant of claim 3, wherein interaction of the wedge structure and the ramp structure of the one or more of the superior member and the inferior member as the wedge structure is translated causes adjustment of the separation of the superior member and the inferior member.

5. The expandable intervertebral implant of claim 3, wherein the superior member is coupled to the inferior member through the wedge structure and the ramp structure of the one or more of the superior member and the inferior member.

6. The expandable intervertebral implant of claim 1, wherein the expansion mechanism disposed between the superior member and the inferior member is also configured to selectively translate the superior member with respect to the inferior member.

7. An expandable intervertebral implant having a first external surface and a second external surface opposite the first external surface, the first and second external surfaces for engaging vertebral matter in-situ, the implant comprising:
a first intervertebral member including a friction structure defining the first external surface of the implant and a first expansion structure opposite the first external surface, the first expansion structure including:
a pair of parallel first rails, a midpoint of the first rails offset from a central axis of the first intervertebral member corresponding to a major axis of a screw that runs through the implant;
a first stabilizing flange; and
a first cut-away section defined in the first intervertebral member such that the first stabilizing flange and first cut-away section are on opposite sides of the central axis of the first intervertebral member;
a second intervertebral member including a friction structure defining the second external surface of the implant and a second expansion structure opposite the second external surface, the second expansion structure including:
a pair of parallel second rails, a midpoint of the second rails offset from a central axis of the second intervertebral member corresponding to the major axis of the screw that runs through the implant;
a second stabilizing flange slidable in the first cut-away section; and
a second cut-away section defined in the second intervertebral member such that the second stabilizing flange and second cut-away section are on opposite sides of the central axis of the second intervertebral member, the first stabilizing member slidable in the second cut-away section, wherein
the first and second intervertebral members are movable relative to each other from an unexpanded configuration to variably spaced configurations as the first stabilizing member slides in the second cut-away section and the second stabilizing flange slides in the first cut-away section, and
the first rails are nested with the second rails in the unexpanded configuration such that each first rail is adjacent a second rail.

8. The expandable intervertebral implant of claim 7, wherein the first and second intervertebral members are interchangeable.

9. The expandable intervertebral implant of claim 7, further comprising a wedge structure that is translated between the first intervertebral member and the second intervertebral member.

* * * * *